United States Patent
Kim et al.

(10) Patent No.: US 9,107,596 B2
(45) Date of Patent: Aug. 18, 2015

(54) METHOD AND APPARATUS FOR MEASURING A BIOLOGICAL SIGNAL

(75) Inventors: Jong-pal Kim, Yongin-si (KR); Seok Chan Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1093 days.

(21) Appl. No.: 13/165,326

(22) Filed: Jun. 21, 2011

(65) Prior Publication Data

US 2012/0004563 A1    Jan. 5, 2012

(30) Foreign Application Priority Data

Jul. 5, 2010    (KR) ........................ 10-2010-0064391

(51) Int. Cl.
| | |
|---|---|
| *A61B 5/04* | (2006.01) |
| *A61B 5/0402* | (2006.01) |
| *A61B 5/00* | (2006.01) |

(52) U.S. Cl.
CPC .............. *A61B 5/0402* (2013.01); *A61B 5/721* (2013.01); *A61B 2560/0247* (2013.01); *A61B 2562/0219* (2013.01)

(58) Field of Classification Search
CPC ................. A61B 5/0402; A61B 5/721; A61B 2560/0247; A61B 2562/0219
USPC .......... 600/509, 513, 309, 345, 300, 528, 547
See application file for complete search history.

(56) References Cited

U.S. PATENT DOCUMENTS

| | | | | |
|---|---|---|---|---|
| 5,109,862 | A * | 5/1992 | Kelen et al. ................... | 600/515 |
| 5,704,365 | A * | 1/1998 | Albrecht et al. .............. | 600/515 |
| 5,908,393 | A * | 6/1999 | Albrecht et al. .............. | 600/509 |
| 2008/0319331 | A1* | 12/2008 | Zizzo et al. ................... | 600/511 |
| 2009/0171228 | A1* | 7/2009 | Fischell et al. ................ | 600/517 |
| 2011/0306892 | A1* | 12/2011 | Kim et al. ..................... | 600/509 |

FOREIGN PATENT DOCUMENTS

| | | |
|---|---|---|
| JP | 08-256998 | 10/1996 |
| JP | 11-318829 | 11/1999 |
| JP | 2001-008914 | 1/2001 |
| JP | 2010-051822 | 3/2010 |
| KR | 10-2007-0039228 | 4/2007 |

\* cited by examiner

*Primary Examiner* — Catherine Voorhees
*Assistant Examiner* — Roland Dinga
(74) *Attorney, Agent, or Firm* — NSIP Law

(57) ABSTRACT

Provided is an apparatus and method for analyzing a biological signal. The apparatus may measure the biological signal, detect a noise signal influencing the electrical characteristics of the measured biological signal, and display the measured biological signal by distinguishing a normal section of the measured biological signal from an abnormal section of the biological signal.

9 Claims, 5 Drawing Sheets

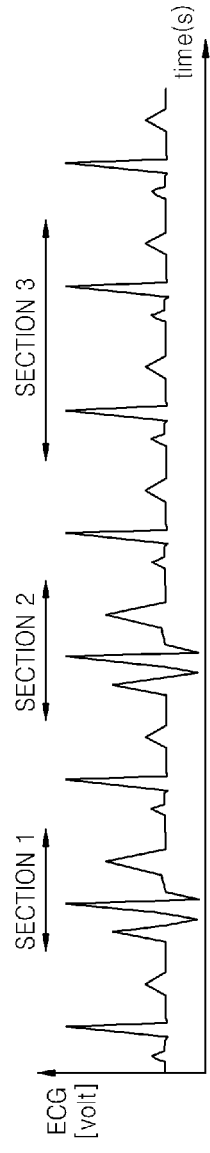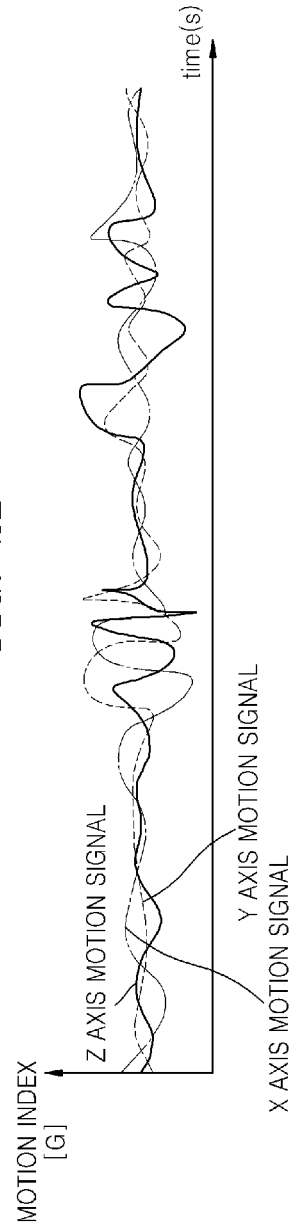

METHOD AND APPARATUS FOR MEASURING A BIOLOGICAL SIGNAL

CROSS-REFERENCE TO RELATED APPLICATION(S)

This application claims the benefit under 35 U.S.C. §119(a) of Korean Patent Application No. 10-2010-0064391, filed on Jul. 5, 2010, in the Korean Intellectual Property Office, the entire disclosure of which is incorporated herein by reference for all purposes.

BACKGROUND

1. Field

The following description relates to an apparatus and method for measuring a biological signal.

2. Description of the Related Art

Various medical devices are in use or are being developed to diagnose a patient's health condition. Medical devices for measuring electrical biological signals, for example, an electrocardiography (ECG) signal, a brain wave signal, an electromyogram signal, and the like, have been important in providing convenience to people. For example, the medical devices provide a prompt health diagnosis result, and the like, during the health diagnosis processes. Such biological signals have electrical characteristics that can be monitored through a display device, such as a monitor of a medical device.

SUMMARY

In one general aspect, there is provided a method for analyzing a biological signal, the method including measuring the biological signal via at least one interface adhered to a person, detecting a noise signal influencing the electrical characteristics of the measured biological signal using at least one sensor adhered to the person, in response to the measured biological signal having an abnormal section, determining whether the abnormal section is caused by the detected noise signal or an abnormal body activity, and displaying the measured biological signal in which a normal section of the measured biological signal is distinguished from the abnormal section thereof.

The biological signal may be displayed by distinguishing an abnormal section of the biological signal caused by the detected noise signal from an abnormal section of the biological signal caused by an abnormal body activity.

The determining may comprise determining whether the measured biological signal has the abnormal section, in response to the measured biological signal having the abnormal section, comparing a noise index calculated using the detected noise signal with a threshold, and determining a cause of the abnormal section according to the comparison result.

The method may further comprise calculating the noise index using the detected noise signal.

The determining of the cause of the abnormal section may comprise, in response to the comparing determining that the noise index exceeds the threshold, determining that the abnormal section is caused by the noise signal, and in response to the comparing determining that the noise index is below the threshold, determining that the abnormal section is caused by an abnormal body activity.

The at least one sensor may comprise an accelerometer sensor, and the displaying of the measured biological signal may comprise displaying information about a direction in which the at least one sensor is adhered to a person obtained using the accelerometer sensor.

The method may further comprise measuring an exercise intensity of the person's body during the measuring of the biological signal, wherein the displaying of the measured biological signal comprises displaying information about a variation in the exercise intensity of the person's body according to a temporal variation of the displayed biological signal.

The biological signal may be the person's electrocardiography (ECG) signal, and the noise signal may comprise at least one of a signal generated according to the person's motion and a motion generated according to a variation of the electrical characteristics of the at least one interface due to an external factor.

The method may further comprise storing the measured biological signal and the detected noise signal in a storage unit, wherein the determining comprises determining the cause of the abnormal section by obtaining the biological signal and the noise signal stored in the storage unit.

In another aspect, there is provided a computer readable storage medium having stored therein program instructions to cause a processor to implement a method for analyzing a biological signal, the method including measuring the biological signal via at least one interface adhered to a person, detecting a noise signal influencing the electrical characteristics of the measured biological signal using at least one sensor adhered to the person, in response to the measured biological signal having an abnormal section, determining whether the abnormal section is caused by the detected noise signal or an abnormal body activity, and displaying the measured biological signal in which a normal section of the measured biological signal is distinguished from the abnormal section thereof.

In another aspect, there is provided an apparatus for analyzing a biological signal, the apparatus including an interface unit configured to be adhered to a person and for measuring the biological signal from the person, a noise detecting unit configured to be adhered to the person and comprising at least one sensor for detecting a noise signal influencing the electrical characteristics of the measured biological signal, a determining unit for determining whether the abnormal section is caused by the detected noise signal or an abnormal body activity, and a display unit for displaying the measured biological signal in which a normal section of the measured biological signal is distinguished from the abnormal section thereof.

The biological signal may be displayed by distinguishing an abnormal section of the biological signal caused by the detected noise signal from an abnormal section of the biological signal caused by an abnormal body activity.

The determining unit may comprise a determining unit for determining whether the measured biological signal has the abnormal section, a comparing unit for comparing a noise index calculated using the detected noise signal with a threshold, and a noise determining unit for determining a cause of the abnormal section based on the comparison result.

The apparatus may further comprise a noise processing unit for calculating the noise index using the detected noise signal The display unit may display at least one of information about a direction in which the at least one sensor is adhered and information about a variation in an exercise intensity of the person's body during measuring of the biological signal.

The apparatus may further comprise a storage unit for storing the measured biological signal and the detected noise signal, wherein the determining unit determines the cause of the abnormal section by obtaining the biological signal and the noise signal stored in the storage unit.

The interface unit and the noise detecting unit may be included in a different device connected to the determining unit and the display unit over a wired or wireless network.

In another aspect, there is provided a device for displaying a measured biological signal, the device including a determining unit for determining whether an abnormal section of a measured biological signal is caused by a noise signal or by an abnormal body activity, and a display unit for displaying the measured biological signal in which an abnormal section caused by the noise signal is distinguished from an abnormal section caused by the abnormal body activity.

The device may further comprise a noise processing unit for calculating a noise index using the detected noise signal, wherein the determining unit determines whether the abnormal section is caused by the noise signal or by the abnormal body activity by comparing the calculated noise index with a threshold.

The device may further comprise a receiver configured to wirelessly receive data about the biological signal and the noise signal measured from a person.

The receiver may be configured to receive the biological signal wirelessly from an interface unit that is configured to be adhered to a person.

The biological signal may be a person's electrocardiography (ECG) signal, and the noise signal may comprise a motion signal generated according to a motion of the person.

Other features and aspects will be apparent from the following detailed description, the drawings, and the claims.

BRIEF DESCRIPTION OF THE DRAWINGS

FIG. 2A is a graph illustrating an example of a biological signal measured by an interface unit.

FIG. 2B is a graph illustrating an example of a noise signal detected by a noise detecting unit.

Figure 1:
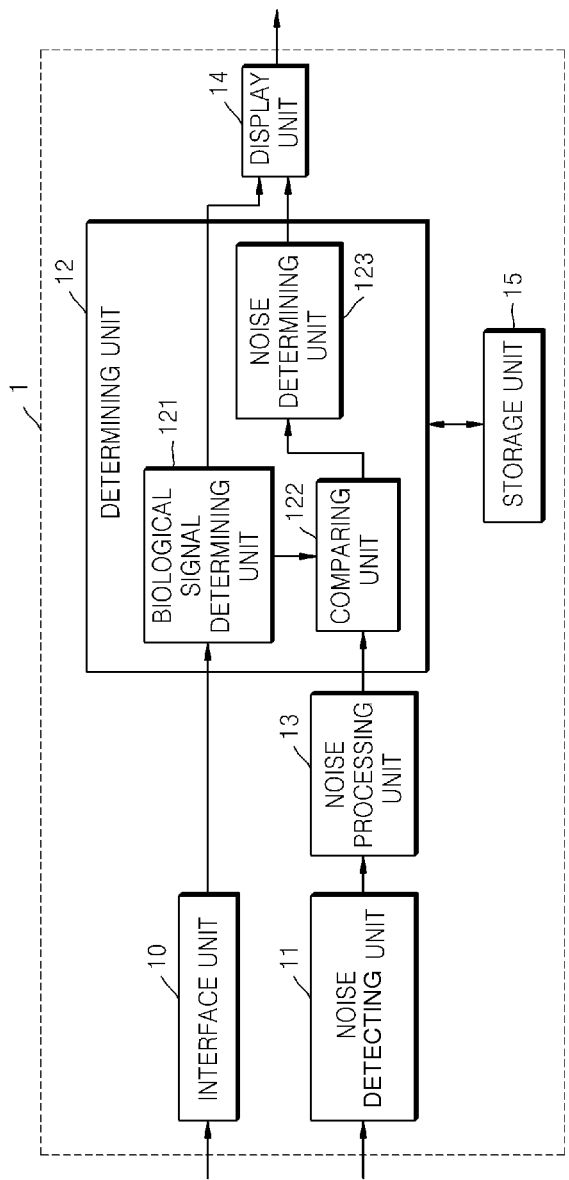
FIG. 1 is a diagram illustrating an example of an apparatus for measuring a biological signal.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. Also, descriptions of well-known functions and constructions may be omitted for increased clarity and conciseness.

FIG. 1 illustrates an example of an apparatus for measuring a biological signal.

Referring to FIG. 1, apparatus 1 for measuring the biological signal ("apparatus 1") includes an interface unit 10, a noise detecting unit 11, a determining unit 12, a noise processing unit 13, a display unit 14, and a storage unit 15. In this example, the determining unit 12 includes a biological signal determining unit 121, a comparing unit 122, and a noise determining unit 123. The determining unit 12 and the noise processing unit 13 may be a processor. The processor may include, for example, an array of logic gates, or a combination of a general-use microprocessor and a memory in which a program to be executed in the general-use microprocessor is stored.

The apparatus 1 shown in FIG. 1 is an example, and may include various forms based on the elements illustrated in FIG. 1.

The apparatus 1 includes medical devices and equipment used to measure the biological signal. For example, the apparatus 1 may include an electroencephalograph, an apparatus for analyzing a brain wave signal, a retinal electrometer, a sphygmograph, an apparatus for monitoring a parturition, a thermograph, a slit lamp microscope, an extensometer, a phonocardiograph, an electrocardiograph, a clinical thermometer, a scale, an ultrasonic blood flowmeter, a sphygmomanometer, a blood glucose meter, a spirometer, and/or the like. For example, the biological signal may include a brain wave signal, an electrocardiography (ECG) signal, an electromyogram signal, a body temperature, a body weight, an obesity index, a fat mass, a liver value, a cholesterol value, a blood glucose level, the number of heartbeats, an oxygen saturation, and/or the like.

For purposes of description herein, the apparatus 1 is described as an apparatus for measuring a person's ECG signal, but it should be appreciated that the apparatus 1 is not limited thereto. The biological signal may include any biological signals that can be electrically detected from a person, such as a brain wave signal, an electromyogram signal, and the like. The above-mentioned biological signals may be measured by a single device.

The interface unit 10 may be adhered to a person and may measure the biological signal of the person. The interface unit 10 includes at least one interface. If the measured biological signal includes an ECG signal, each interface of the interface unit 10 may correspond to an electrode.

The ECG signal may be displayed in graph form and may represent electrical activity of the heart of a person. For example, when heart muscles of the heart of the person contract and expand, a current spreading from the heart of the person to the body of the person is generated. The current causes a potential difference to form between different parts of the body of the person. The potential difference may be obtained by the interface unit 10 adhered to or placed near the skin of the person. For example, the electrical activity of the heart of the person may be identified according to changes in the obtained potential difference.

The ECG signal may be measured using the characteristic that electric potentials between the heart of the person and different parts of the body of the person are different from each other. As an example, the ECG signal may be detected by adhering interfaces, like a pair of electrodes, to two different parts of the skin of the person, and measuring a potential difference between the electrodes over a predetermined period of time. For example, the measured potential difference between the electrodes may be expressed as a signal in wave form repeatedly rising and falling over time. The ECG signal may be displayed on the display unit 13 as a wave line.

The interface unit 10 for electrically interfacing the body of the person may include a wet type electrode, a dry type electrode, an insulation type electrode, a probe type electrode, and/or the like. For example, an insulation type electrode may use static coupling, thereby electrically interfacing a person's skin by being placed near the person's skin, without contacting the person's skin. The interface unit 10 may include individual elements that are separated from each other or individual elements partially or wholly included in the same element.

The noise detecting unit 11 may be adhered to a person and may detect a noise signal influencing the electrical characteristics of the biological signal using at least one sensor. For example, the noise detecting unit 11 may include at least one sensor for detecting the noise signal. The noise signal may include at least one of a motion signal generated according to motion of the person and a motion artifact generated according to a variation of the electrical characteristics of the interface unit 10 due to an external factor.

For example, the motion signal may be a noise signal indicating a direction of motion of the person, the size thereof, and the like, and influencing the electrical characteristics of the biological signal. The motion signal may be detected using an accelerometer sensor for measuring acceleration along at least one axis. For example, if a one-axis accelerometer sensor or a three-axis accelerometer sensor is used, the motion signal may be detected in a sensing axis direction along an axis disposed in a direction corresponding to the length of the person, or in sensing axis directions along X, Y, and Z axes.

When the interface unit 10 adhered to the person measures the biological signal, the biological signal may be influenced by the motion signal. As mentioned above, the interface unit 10 may interface the skin of the person and may measure the biological signal by contacting the skin of the person or by being placed near the skin of the person without contacting the skin of the person. Therefore, if the person moves while the interface unit 10 interfaces the skin of the person, an electromyogram signal and a distribution of charges between the interface unit 10 and the skin of the person may temporarily vary in response to the movement. Accordingly, the electrical characteristics of the biological signal may vary according to the variations of the electromyogram signal and the distribution of charges. Such variation of the electrical characteristics of the biological signal may make it difficult for the biological signal to be precisely monitored.

The motion artifact may be a noise signal influencing the electrical characteristics of the biological signal due to, for example, a variation in impedances of the interfaces of the interface unit 10, twisting of the interfaces, strain due to change of shape of the interfaces, a variation in pressure applied to the interfaces, variations in the optical characteristics of the interfaces, and the like, such as when an external force is applied to the interfaces due to motion of the person. Like the motion signal, the variation of the electrical characteristics of the biological signal may make it difficult for the biological signal to be precisely monitored.

For example, the noise detecting unit 11 may simultaneously detect the motion signal and the motion artifact using the accelerometer sensor. As another example, the noise detecting unit 11 may detect the motion signal using the accelerometer sensor and may detect the motion artifact using other sensors, such as a strain gauge, a piezoelectric device, and the like.

FIG. 2A illustrates an example of a biological signal measured by an interface unit.

Referring to FIG. 2A, the graph shows a variation of an ECG signal according to time elapsed. In this example, a waveform of the ECG signal has three sections 1, 2, and 3 each having a period corresponding to a person's heartbeat. The wave forms of the sections 1 and 2 are different from that of the section 3. This may be because the ECG signal is abnormal in the sections 1 and 2. For example, the abnormal ECG signal may be due to a noise signal such as a motion signal or a motion artifact, or an abnormal body activity such as an arrhythmia. Therefore, it is necessary to distinguish the abnormal waveforms of the sections 1 and 2 from the normal waveform of the section 3 in order to precisely monitor the biological signal.

FIG. 2B illustrates an example of a noise signal detected by a noise detecting unit.

Referring to FIG. 2B, the graph shows variations of a motion signal with respect to each axis according to time elapsed. In this example, a three-axis accelerometer sensor is used to detect the motion signal by measuring acceleration along X, Y, and Z axes. For example, the motion signal may be detected by the noise detecting unit 11 in order to determine whether the noise signal, such as the motion signal, influences a variation in the electrical characteristics of an ECG signal in the sections that have abnormal waveforms like the sections 1 and 2 of FIG. 2A.

Referring again to FIG. 1, the noise processing unit 13 may calculate a noise index using the noise signal detected by the noise detecting unit 11. In the example of a motion signal, the noise index may be calculated as the absolute value of an acceleration vector along detected axes. When the noise detecting unit 11 uses the three-axis accelerometer sensor for detecting acceleration along X, Y, and Z axes of FIG. 2B, the noise processing unit 13 may calculate the absolute value of the acceleration vector by setting weights of all axes as 1. The noise processing unit 13 may calculate the absolute value of the acceleration vector by setting a weight of a sensing axis in a direction corresponding to the length of the person to be greater than that of another sensing axis. The noise index, such as the absolute value of the acceleration vector calculated by the noise processing unit 13, may be used to determine an influence on the electrical characteristics of the biological signal, such as the ECG signal measured by the interface unit 10.

When the measured biological signal has an abnormal section, the determining unit 12 may determine whether the abnormal section is caused by the detected noise signal or an abnormal body activity. For example, the determining unit 12 may determine a cause for the abnormal section of the measured biological signal. As described above, in this example the determining unit 12 includes the biological signal determining unit 121, the comparing unit 122, and the noise determining unit 123.

An example of an abnormal body activity is an arrhythmia. An arrhythmia is a problem with the rate or rhythm of a heartbeat. During an arrhythmia, a heart fails to generate or spread an electrical stimulus and does not regularly contract. This may be an indication that the heart may be beating too quickly, too slowly, or irregularly. The abnormal body activity may cause an abnormal section in the measured ECG signal.

However, when the measured ECG signal is merely displayed and monitored, whether an abnormal section is caused by a noise signal or an abnormal body activity, such as an arrhythmia may not be determined. Thus, if a cause determined by the determining unit 12 and the ECG signal are simultaneously displayed, the ECG signal may be evaluated more efficiently.

The biological signal determining unit 121 may determine whether the measured biological signal has an abnormal section. If the biological signal determining unit 121 determines that the measured biological signal has no abnormal sections, the measured biological signal is determined to be normal and is displayed on the display unit 14. However, if the biological signal determining unit 121 determines that the measured biological signal has at least one abnormal section, the comparing unit 122 and/or the noise determining unit 123 may determine the cause of the abnormal section.

The biological signal determining unit 121 may use various methods for determining whether the measured biological signal has an abnormal section. For example, the storage unit 15 may previously store shapes of a normal waveform and an abnormal waveform of an ECG signal. When the measured ECG signal is transmitted from the interface unit 10, the biological signal determining unit 121 may compare the shapes of the normal waveform and the abnormal waveform of the ECG signal stored in the storage unit 15 with the shapes of a waveform of the measured ECG signal of each section. As a result of the comparison, a section of the ECG signal that has a waveform that corresponds to the shape of the normal waveform of the ECG signal stored in the storage unit 15 is determined as a normal section of the measured ECG signal. A section of the ECG signal that has a waveform that corresponds to the shape of the abnormal waveform of the ECG signal stored in the storage unit 15 is determined as an abnormal section of the measured ECG signal. It should be appreciated that the biological signal determining unit 121 is not limited to the method described above and alternative examples thereof may use other methods of determining whether the measured biological signal has an abnormal section.

If the biological signal determining unit 121 determines that the measured biological signal has an abnormal section, the comparing unit 122 may compare the noise index using the detected noise signal calculated by the noise processing unit 13 with a threshold. For example, the threshold may be previously set when manufacturing the apparatus 1. As another example, the threshold may be changed by a user. The comparison of the noise index and the threshold in the comparing unit 122 may be used to determine whether the abnormal section is caused by the noise signal.

According to the comparison result, the noise determining unit 123 may determine the cause of an abnormal section. For example, if the comparing unit 122 determines that the noise index exceeds the threshold, the noise determining unit 123 may determine that the abnormal section is caused by the detected noise signal. As another example, if the comparing unit 122 determines that the noise index is below the threshold, the noise determining unit 123 may determine that the abnormal section is caused by an abnormal body activity. As another example, if the comparing unit 122 determines that the noise index is the same as the threshold, a user may set whether the detected noise signal or an abnormal body activity is the cause.

The display unit 14 may display the measured biological signal while displaying the determination result of the determining unit 12 such that abnormal sections of the measured biological signal are distinguished from normal sections thereof. For example, the display unit 14 may display the measured biological signal while distinguishing an abnormal section caused by the noise signal from an abnormal section caused by an abnormal body activity. Accordingly, the ECG signal and the cause of an abnormal section of the ECG signal may be simultaneously monitored.

For example, abnormal sections of the measured biological signal may be distinguished from a normal section by changing any of color, thickness, pattern, a background color, and the like, of waveforms of the ECG signal in the abnormal sections. As another example, the abnormal sections may be distinguished using an arrow. As another example, when the abnormal sections of the measured biological signal have different causes, each of the different causes may be associated with a different color, thickness, pattern, background color, and the like, to distinguish the abnormal sections of the measured biological signal from each other.

As another example, the display unit 14 may display information about a direction in which each accelerometer sensor of the noise detecting unit 11 is adhered. When each of the interfaces of the interface unit 10 is manufactured to be adjacent or is adhered to each accelerometer sensor of the noise detecting unit 11, a direction in which each interface of the interface unit 10 is adhered may be obtained through the direction in which each accelerometer sensor of the noise detecting unit 11 is adhered. For example, the direction in which each accelerometer sensor of the noise detecting unit 11 is adhered may be obtained from an angle between each accelerometer sensor and a direction of gravity. For example, the angle indicating the direction in which each accelerometer sensor of the noise detecting unit 11 is adhered may be a value obtained by dividing a measured acceleration value of a sensing axis of each accelerometer sensor by acceleration of gravity. The information about the direction in which each accelerometer sensor of the noise detecting unit 11 is adhered may be displayed on the display unit 14 using an angle such as 45 or 90 degrees.

As another example, the display unit 14 may display information about a variation in the intensity at which the person wearing the sensor exercises when measuring the biological signal. For example, the display unit 14 may display the information about the variation in the intensity according to a temporal variation of the biological signal. As an example, the variation in the intensity may correspond to a variation in a cycle of a heartbeat, a variation in the size of the motion signal measured by each accelerometer sensor of the noise detecting unit 11, and the like.

Figure 3:
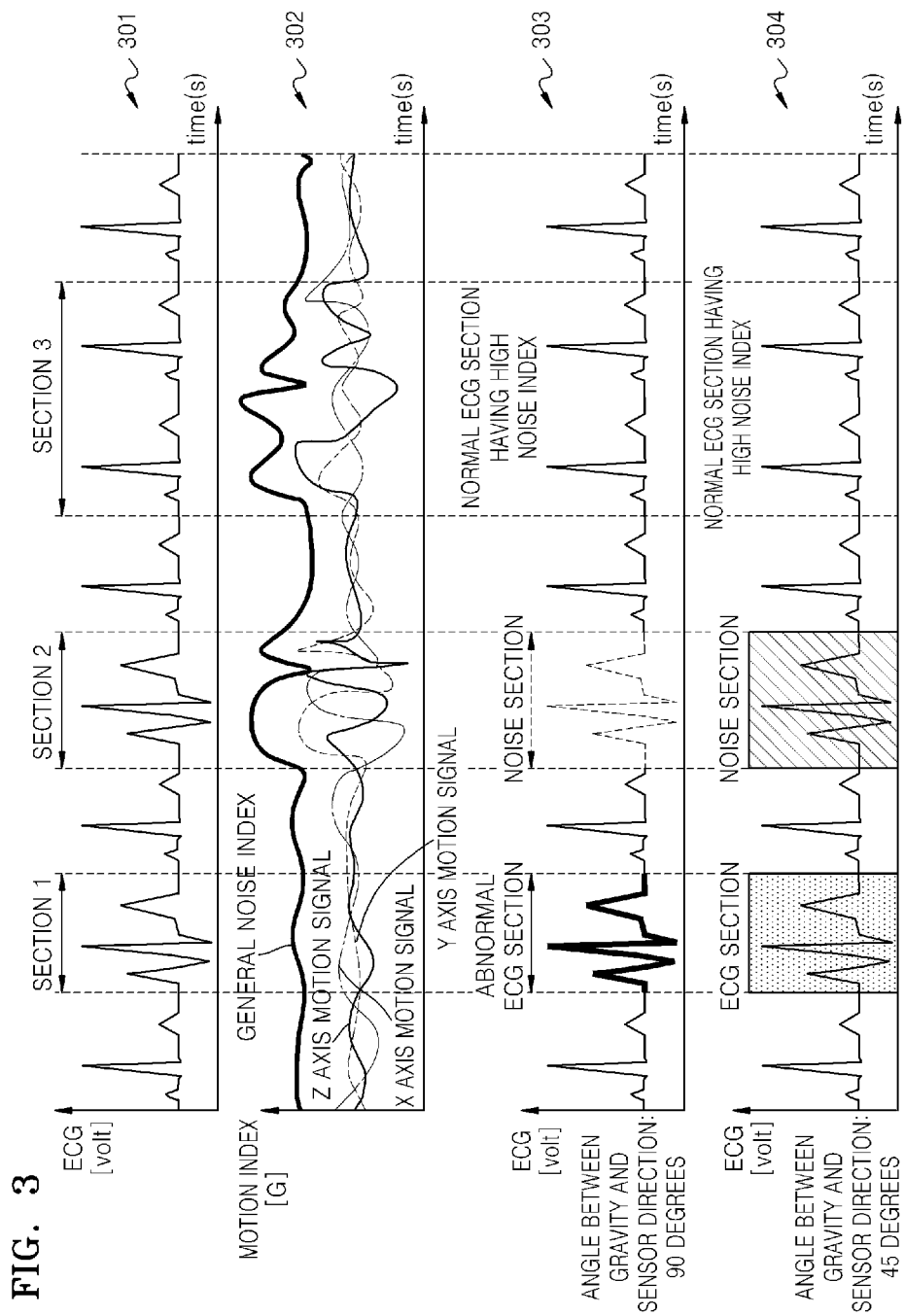
FIG. 3 is a diagram illustrating an example of a biological signal displayed on a display unit.

FIG. 3 illustrates an example of a biological signal displayed on a display unit.

Referring to FIG. 3, the biological signal includes a waveform 301 corresponding to the ECG signal that may be measured by the interface unit 10, a waveform 302 indicating the motion signal that may be detected by the noise detecting unit 11, and waveforms 303 and 304 of examples of the ECG signal that may be the determination result of the determining unit 12. The display unit 14 may simultaneously display the waveform 301 corresponding to the measured ECG signal, the waveform 302 indicating the motion signal, and the waveforms 303 and 304 of examples of the ECG signal reflecting the determination result. As another example, the display unit may display the waveforms 303 and 304 of examples of the ECG signal reflecting the determination result only.

The ECG signal measured by the interface unit 10 may include abnormal sections 1 and 2. For example, the biological signal determining unit 121 may determine that the sections 1 and 2 are abnormal. The comparing unit 122 may compare a noise index in each of the sections 1 and 2 with a threshold.

As a result of comparison, the noise index may be determined to be below the threshold in the section 1, and thus the noise determining unit 123 may determine that the section 1 is abnormal due to an abnormal body activity such as an arrhythmia. As another example, the noise index may be determined to exceed the threshold in the section 2, and thus the noise determining unit 123 may determine that the section 2 is abnormal due to a noise signal.

For example, section 3 may have a relatively high noise index, and the biological signal determining unit 121 may determine that the section 3 is normal. This may be because influences of motion signals of each axis are offset to the ECG signal in the section 3 and thus the ECG signal is a normal signal in the section 3.

As shown in the waveform 303 of the ECG signal indicating the determination result, section 1 is determined to be caused by an abnormal body activity, and the display unit 14 may display the section 1 as a bold full line unlike a normal section. Because section 2 is determined to be caused by a noise signal, the display unit 14 may display the section 2 as a dotted line unlike the normal section and the section 1. As shown in the waveform 304 of the ECG signal indicating the determination result, section 1 is determined to be caused by an abnormal body activity, and the display unit 14 may display a gray background color in the section 1 unlike the normal section. Because the section 2 is determined to be caused by a noise signal, the display unit 14 may display a deviant crease line background in the section 2 unlike the normal section and the section 1. The various examples of waveforms shown in FIG. 3 are merely for purposes of example, and it should be understood the displaying of the waveforms is not limited thereto.

As described above, a method of distinguishing the sections 1 and 2 and a normal section from each other and displaying the sections 1 and 2 and the normal section may be changed, for example, based on a user's use environment, a user's preference, and the like.

Furthermore, like the waveforms 303 and 304 of examples of the ECG signal indicating the determination result, the display unit 14 may display directions in which the interface unit 10 and the noise detecting unit 11 are adhered using an angle such as 45 or 90 degrees.

Figure 4:
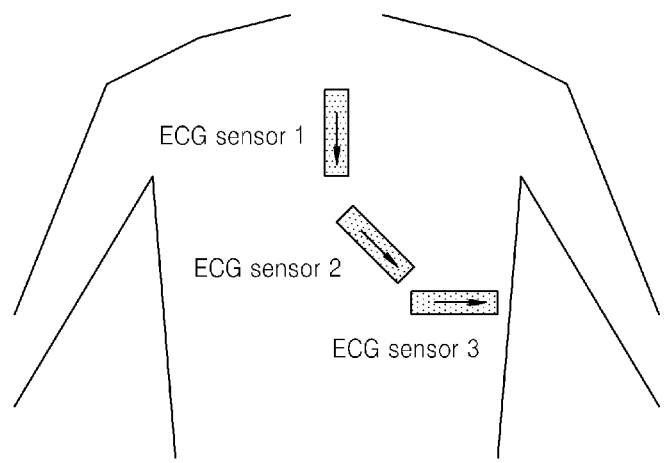
FIG. 4 is a diagram illustrating an example of different directions in which interfaces may be adhered.

FIG. 4 illustrates an example of different directions in which interfaces may be adhered.

In this example, the interfaces are adhered to a person in multiple directions to measure ECG signals according to the directions to which the interfaces are adhered. As described above, for example, the directions in which interfaces are adhered may be measured using an accelerometer sensor, and the display unit 14 may display information about the directions in which interfaces are adhered.

Referring again to FIG. 1, the interface unit 10 and the noise detecting unit 11 may be included in another device that is connected to the determining unit 12, the noise processing unit 13, and the display unit 14, over a wired or wireless network. For example, the interface unit 10 and the noise detecting unit 11 may be included in a device adhered to a person's skin, and one or more of the determining unit 12, the noise processing unit 13, and/or the display unit 14 may be included in another device, and the determining unit 12, the noise processing unit 13, and/or the display unit 14 may communicate with the interface unit 10 and the noise detecting unit 11 over a wired or wireless network and receive the measured biological signal and the noise signal. As another example, the interface unit 10, the noise detecting unit 11, the determining unit 12, the noise processing unit 13, and the display unit 14 may be included in a single device and adhered to the person's skin.

For example, a first device may include the noise detecting unit 11 and/or the interface unit 10 and may also include a transmitter and/or a receiver to transmit and/or receive data to a second device that may include one or more of the determining unit 12, the noise processing unit 13, and/or the display unit 14. The second device may also include a transmitter and/or a receiver to receive the data from the first device.

As another example, a first device may include the interface unit, the noise detecting unit 11, and the noise processing unit 13, and a second device may include the determining unit 12 and the display unit 14. Each device may also include transmitters and/or receivers to transmit and receive data.

The storage unit 15 may store the measured biological signal and noise signal. In addition, the storage unit 15 may store data that has been processed and data that is to be processed by the apparatus 1, such as the determination result of the determining unit 12.

The apparatus 1 may measure the biological signal from the person, detect the noise signal, analyze the biological signal and the noise signal in real time, and display the analysis. For example, the apparatus 1 may obtain the data stored in the storage unit 15, that is, the measured biological signal and the detected noise signal, as desired by a user, analyze the data, and display the analysis for the user.

Figure 5:
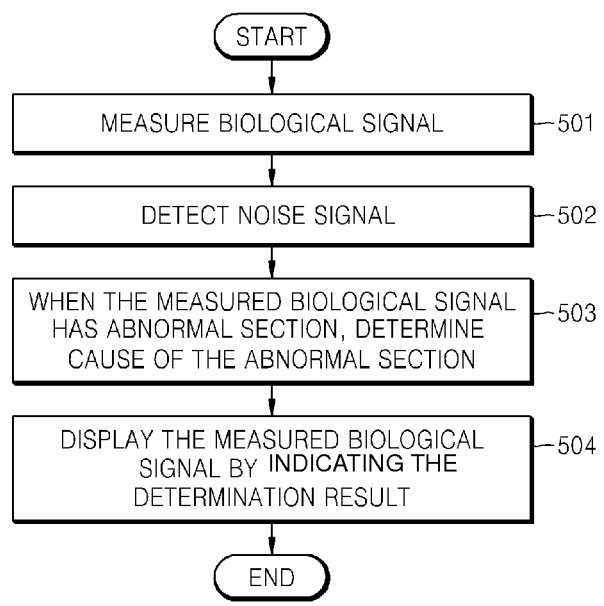
FIG. 5 is a flowchart illustrating an example of a method for analyzing a biological signal.

FIG. 5 illustrates an example of a method for analyzing a biological signal.

Referring to FIG. 5, the method of analyzing the biological signal may include operations time-serially processed by the apparatus 1 of FIG. 1. For example, although not described, the description above regarding the apparatus 1 of FIG. 1 applies to the method of analyzing the biological signal of the present example.

In 501, the interface unit 10 is adhered to a person and measures a biological signal of the person. In 502, the noise detecting unit 11 is adhered to the person and detects a noise signal influencing the electrical characteristics of the measured biological signal. In 503, when the measured biological signal has an abnormal section, the determining unit 12 determines whether the abnormal section is caused by the detected noise signal or an abnormal body activity. In 504, the display unit 14 displays the measured biological signal while also displaying the determination result in such a way that a normal section of the measured biological signal is distinguished from the abnormal section.

Figure 6:
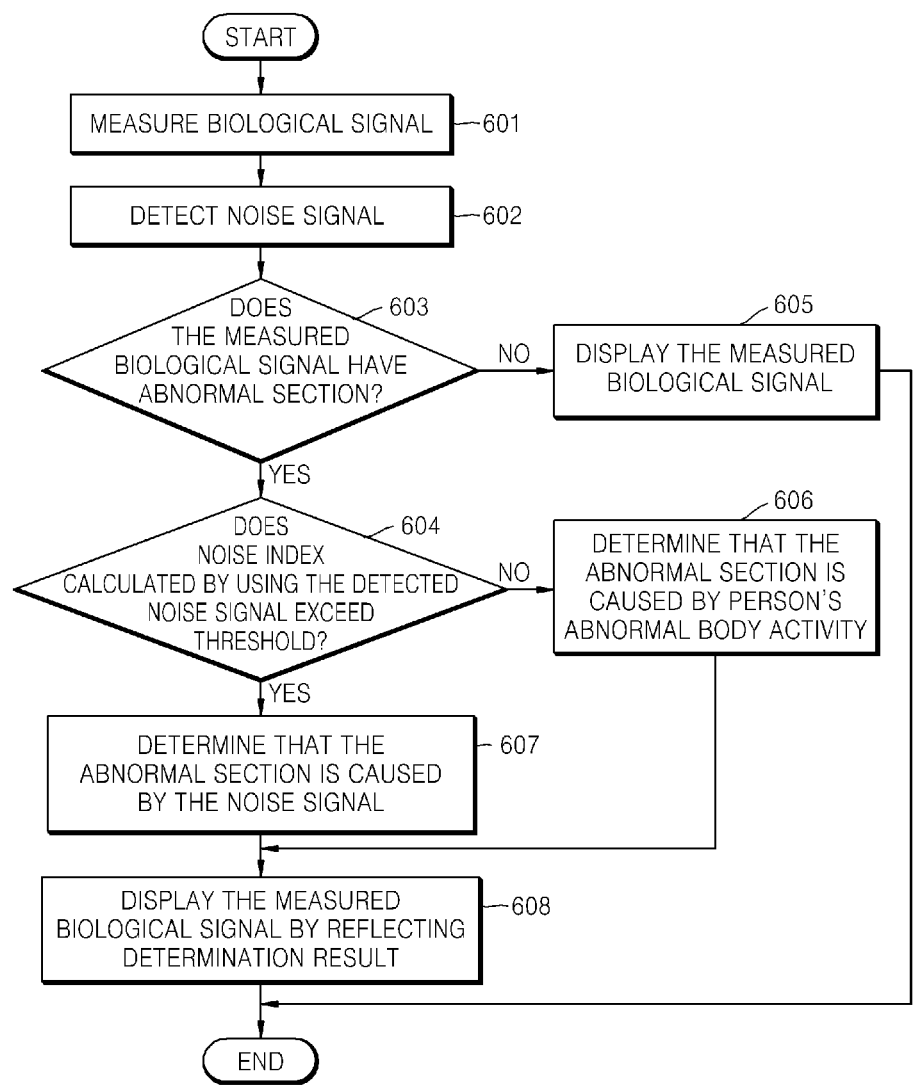
FIG. 6 is a flowchart illustrating an example of another method for analyzing a biological signal.

FIG. 6 illustrates another example of method for analyzing a biological signal.

Referring to FIG. 6, in 601, the interface unit 10 is adhered to a person and measures a biological signal of the person. In 602, the noise detecting unit 11 is adhered to the person and detects a noise signal that influences the electrical characteristics of the measured biological signal. In 603, the biological signal determining unit 121 determines whether the measured biological signal has an abnormal section.

If the measured biological signal has an abnormal section, in 604, the comparing unit 122 compares a noise index calculated using the detected noise signal with a threshold. If the measured biological signal does not have an abnormal section, in 605, the display unit 14 displays the measured biological signal. If the noise index is less than or equal to the threshold, in 606, the noise determining unit 123 determines that the abnormal section is caused by an abnormal body activity. If the noise index is greater than the threshold, in 607, noise determining unit 123 determines that the abnormal section is caused by the noise signal. In 608, the display unit 14 displays the measured biological signal by reflecting the determination result.

As described above, using the apparatus 1 for measuring the biological signal and the method of analyzing the biological signal, a person's biological signal is measured and displayed by identifying an influenced abnormal section, such as noise, of the biological signal, and thus a user can more precisely monitor the biological signal to determine whether an abnormal section of a signal is the result of noise or whether it is the result of an abnormal body condition of the person wearing the sensor.

The processes, functions, methods, and/or software described herein may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for analyzing a biological signal, the method comprising:
    measuring the biological signal via at least one interface;
    detecting a noise signal influencing electrical characteristics of the measured biological signal using at least one sensor;
    in response to the measured biological signal having an abnormal section, determining whether the abnormal section is caused by the detected noise signal or an abnormal body activity; wherein the determining step comprises comparing a noise index calculated using the detected noise signal with a threshold; and determining a cause of the abnormal section according to the comparison result; and
    displaying the measured biological signal in which a normal section of the measured biological signal is distinguished from the abnormal section.

2. The method of claim 1, wherein the biological signal is displayed by distinguishing an abnormal section of the biological signal caused by the detected noise signal from an abnormal section of the biological signal caused by an abnormal body activity.

3. The method of claim 1, further comprising calculating the noise index using the detected noise signal.

4. The method of claim 1, wherein the determining of the cause of the abnormal section comprises, in response to the comparing determining that the noise index exceeds the threshold, determining that the abnormal section is caused by the noise signal, and in response to the comparing determining that the noise index is below the threshold, determining that the abnormal section is caused by an abnormal body activity.

5. The method of claim 1, wherein the at least one sensor comprises an accelerometer sensor, and the displaying of the measured biological signal comprises displaying information about a direction in which the at least one sensor is adhered to a body obtained using the accelerometer sensor.

6. The method of claim 1, further comprising measuring an exercise intensity of a body during the measuring of the biological signal,
    wherein the displaying of the measured biological signal comprises displaying information about a variation in the exercise intensity of the body according to a temporal variation of the displayed biological signal.

7. The method of claim 1, wherein the biological signal is an electrocardiography (ECG) signal, and the noise signal comprises at least one of a signal generated according to the motion of a body and a motion generated according to a variation of the electrical characteristics of the at least one interface due to an external factor.

8. The method of claim 1, further comprising storing the measured biological signal and the detected noise signal in a storage unit,
    wherein the determining comprises determining the cause of the abnormal section by obtaining the biological signal and the noise signal stored in the storage unit.

9. The method of claim 1, further comprising: distinguishing abnormal sections of the measured biological signal based on a different color, thickness, pattern, or background color.

* * * * *